US00PP28344P3

(12) United States Plant Patent
Barbour et al.

(10) Patent No.: US PP28,344 P3
(45) Date of Patent: Aug. 29, 2017

(54) OAK TREE NAMED 'OCHLOCKNEE'

(50) Latin Name: *Quercus nuttallii*
Varietal Denomination: Ochlocknee

(71) Applicants: John Barbour, Hawkinsville, GA (US); Kevin Redeker, Bonaire, GA (US)

(72) Inventors: John Barbour, Hawkinsville, GA (US); Kevin Redeker, Bonaire, GA (US)

(73) Assignee: Athena Trees, Inc., Hawkinsville, GA (US)

( * ) Notice: Subject to any disclaimer, the term of this patent is extended or adjusted under 35 U.S.C. 154(b) by 80 days.

(21) Appl. No.: 14/545,867

(22) Filed: Jun. 30, 2015

(65) Prior Publication Data

US 2017/0006751 P1 Jan. 5, 2017

(51) Int. Cl.
*A01H 5/00* (2006.01)

(52) U.S. Cl.
USPC ..... Plt./225

(58) Field of Classification Search
USPC ..... Plt./225
See application file for complete search history.

(56) References Cited

PUBLICATIONS

Plant Search Online Wholesale plant varieties—*Qiongzhuea* to *Quizqualis* 2014 retrieved on Nov. 22, 2016, retrieved from the Internet at <http://www.plantsearchonline.com/Q.htm> pp. 1-5.*

* cited by examiner

*Primary Examiner* — June Hwu
(74) *Attorney, Agent, or Firm* — C. A. Whealy

(57) ABSTRACT

A new and distinct cultivar of Oak tree named 'Ochlocknee', characterized by its upwardly sweeping lateral branches forming an narrow upright tree form; freely branching habit with numerous secondary branches providing a full and densely foliated appearance; and numerous glossy dark green-colored leaves that become dark purple and orange in color during the autumn.

6 Drawing Sheets

Botanical designation: *Quercus nuttallii.*
Cultivar denomination: 'OCHLOCKNEE'.

BACKGROUND OF THE INVENTION

The present invention relates to a new and distinct cultivar of Oak tree, botanically known as *Quercus nuttallii*, commercially referred to as Nuttall Oak or Red Oak and hereinafter referred to by the name 'Ochlocknee'.

The new Oak tree is a product of a planned breeding program conducted by the Inventors in Pulaski and Oconee Counties, Ga. The objective of the breeding program is to create new Oak trees appropriate for urban landscapes with freely and upswept branching habit and full, densely-foliated appearance.

The new Oak tree originated from an open-pollination of an unnamed selection of *Quercus nuttallii*, not patented, as the female, or seed, parent with an unknown selection of *Quercus nuttallii* as the male, or pollen, parent. The new Oak tree was discovered and selected by the Inventor as a single plant from within the progeny of the stated open-pollination in a controlled environment in Pulaski County, Ga. in November, 2005.

Asexual reproduction of the new Oak tree by softwood cuttings in a controlled environment in Oconee County, Ga. has shown that the unique features of this new Oak tree are stable and reproduced true to type in successive generations.

SUMMARY OF THE INVENTION

Trees of the new Oak have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'Ochlocknee'. These characteristics in combination distinguish 'Ochlocknee' as a new and distinct Oak tree:

1. Upwardly sweeping lateral branches forming an narrow upright tree form.
2. Freely branching habit with numerous secondary branches providing a full and densely foliated appearance.
3. Numerous glossy dark green-colored leaves that become dark purple and orange in color during the autumn.

Trees of the new Oak can be compared to trees of the female parent selection. Trees of the new Oak differ primarily from trees of the female parent selection in branch orientation as lateral branches of trees of the new Oak are more upright than lateral branches of trees of the female parent selection. In addition, trees of the new Oak are more densely-foliated than trees of the female parent selection as trees of the female parent selection produce about two-thirds the number of leaves as trees of the new Oak.

Trees of the new Oak can also be compared to trees of *Quercus nuttallii* 'Big Boy', not patented. Trees of the new Oak and 'Big Boy' differ primarily in the following characteristics:

1. Trees of the new Oak have upwardly sweeping lateral branches forming a narrow upright tree form whereas trees of 'Big Boy' have less upright-orientated lateral branches forming a narrow and more oval tree form.

2. Trees of the new Oak are denser than trees of 'Big Boy' with more secondary lateral branches and producing 93% more leaves than trees of 'Big Boy'.

BRIEF DESCRIPTION OF THE PHOTOGRAPHS

The accompanying colored photographs illustrate the overall appearance of the new Oak tree showing the colors as true as it is reasonably possible to obtain in colored reproductions of this type. Colors in the photographs may differ slightly from the color values cited in the detailed botanical description which accurately describe the colors of the new Oak tree.

The photographs on the first sheet are side perspective views of typical mature trees of 'Ochlocknee' (left) and 'Big Boy' (right) grown during the winter in an outdoor nursery showing the differences in branch angle orientation and overall tree form.

The photographs on the second sheet are close-up views of typical mature trees of 'Ochlocknee' (left) and 'Big Boy' (right) grown during the winter in an outdoor nursery showing the differences in branch angle orientation.

The photographs on the third sheet are side perspective views of typical young trees of 'Ochlocknee' (left) and 'Big Boy' (right) grown during the summer in an outdoor nursery showing the differences in density, fullness and overall tree form.

The photograph on the fourth sheet is a close-up view of the upper surface of typical leaves of 'Ochlocknee' grown during the summer.

The photograph on the fifth sheet is a close-up view of the upper surface of typical leaves of 'Ochlocknee' grown during the autumn.

The photograph on the sixth sheet is a close-up view of typical lateral branches of trees of 'Ochlocknee' (left) and 'Big Boy' (right) grown during the summer in an outdoor nursery showing the differences in branch and foliage number and density.

DETAILED BOTANICAL DESCRIPTION

The aforementioned photographs and following observations, measurements and values describe trees grown in an outdoor nursery in Pulaski County, Ga. and under cultural practices typical of commercial Oak tree production. Young trees used in the photographs and description were four years old and mature trees used in the photographs and description were nine years old. During the production of the trees, average day temperature was 24.5° C. and average night temperature was 11.1° C. In the following description, color references are made to The Royal Horticultural Society Colour Chart, 2007 Edition, except where general terms of ordinary dictionary significance are used.

Botanical classification: *Quercus nuttallii* 'Ochlocknee'.

Parentage:

*Female, or seed, parent*.—Unnamed selection of *Quercus nuttallii*, not patented.

*Male, or pollen, parent*.—Unknown selection of *Quercus nuttallii*, not patented.

Propagation:

*Type*.—By softwood cuttings.

*Time to develop roots, summer*.—About six weeks at temperatures about 32.2° C.

*Time to produce a rooted young plant, summer*.—About ten months at temperatures about 32.2° C.

*Rooting habit*.—Moderately freely branching; medium density.

Tree description:

*Tree form and growth habit*.—Deciduous tree with upwardly sweeping lateral branches forming a narrow upright tree form; freely branching habit with about 31 lateral branches developing per tree; full and densely-foliated appearance; vigorous growth habit; to date, flower initiation and development have not been observed on trees of the new Oak.

*Tree height, young trees*.—About 5.64 meters.

*Tree height, mature trees*.—About 11.6 meters.

*Tree width (spread), young trees*.—About 2.29 meters.

*Tree width (spread), mature trees*.—About 5.9 meters.

*Trunk caliper, young trees*.—About 9.53 cm.

*Trunk caliper, mature trees*.—About 29.2 cm.

*Growth rate, height, young trees*.—About 1.41 meters per year.

*Growth rate, height, mature trees*.—About 1.29 meters per year.

*Growth rate, caliper, young trees*.—About 2.38 cm per year.

*Growth rate, caliper, mature trees*.—About 3.24 cm per year.

*Branch angle orientation*.—Lower canopy branches, about 25° from vertical; upper canopy branches, about 11° from vertical.

*Lateral branch color*.—Immature bark: Close to between 175A and 176A. Mature bark: Close to 201B with random patches, close to 198A.

*Immature bark texture*.—Smooth, glabrous.

*Mature bark texture*.—Smooth, woody.

*Branch lenticels*.—Size: On one-year growth, about 1 mm by 1 mm; on three to four-year old growth, about 2 mm by 0.75 mm. Shape: On one-year growth, circular; on three to four-year old growth, oblong to ovoid. Color: On one-year growth, close to 156A; on three to four-year old growth, close to 156A.

*Dormant leaf buds*.—Length: About 3.5 mm. Diameter: About 2.2 mm. Shape: Triangular with rounded apex. Texture: Slightly pubescent along margins. Color: Close to 200D; pubescence, close to 199C.

*Leaf arrangement*.—Alternate, simple.

*Leaf length*.—About 15.98 cm.

*Leaf width*.—About 10.27 cm.

*Leaf shape*.—Elliptical.

*Leaf apex*.—Acute.

*Leaf base*.—Cuneate and becoming acute with development.

*Leaf margins*.—Entire; deeply four to five-lobed with small teeth and rounded sinuses.

*Leaf venation*.—Pinnate.

*Leaf texture, upper and lower surfaces*.—Smooth, glabrous.

*Leaf luster, upper and lower surfaces*.—Glossy.

*Leaf color*.—When developing, upper surface: Close to 137A; towards the base, close to 143A. When developing, lower surface: Close to 143A. Fully developed, upper surface: Close to between N137A and 139A; in the autumn, close to 183A, 163B and N199D; venation, close to 160A. Fully developed, lower surface: Close to 137B; in the autumn, close to 178B to 178C, 161A and N199D; venation, close to 160D.

*Leaf petioles*.—Length: About 2.49 cm. Diameter: About 1.5 mm. Texture, upper and lower surfaces: Smooth, glabrous. Color, upper surface: Close to 145B. Color, lower surface: Close to 160B.

Temperature tolerance: Trees of the new Oak have been observed to tolerate high temperatures about 40.5° C. and low temperatures about −11.7° C. when grown in USDA Hardiness Zone 8.

Pathogen & pest resistance: Trees of the new Oak have been observed to be resistant to Oak Anthracnose (*Apiognomonia quercina*). Trees of the new Oak have not been observed to be resistant to pests and other pathogens common to Oak trees.

It is claimed:

1. A new and distinct Oak tree named 'Ochlocknee' as illustrated and described.

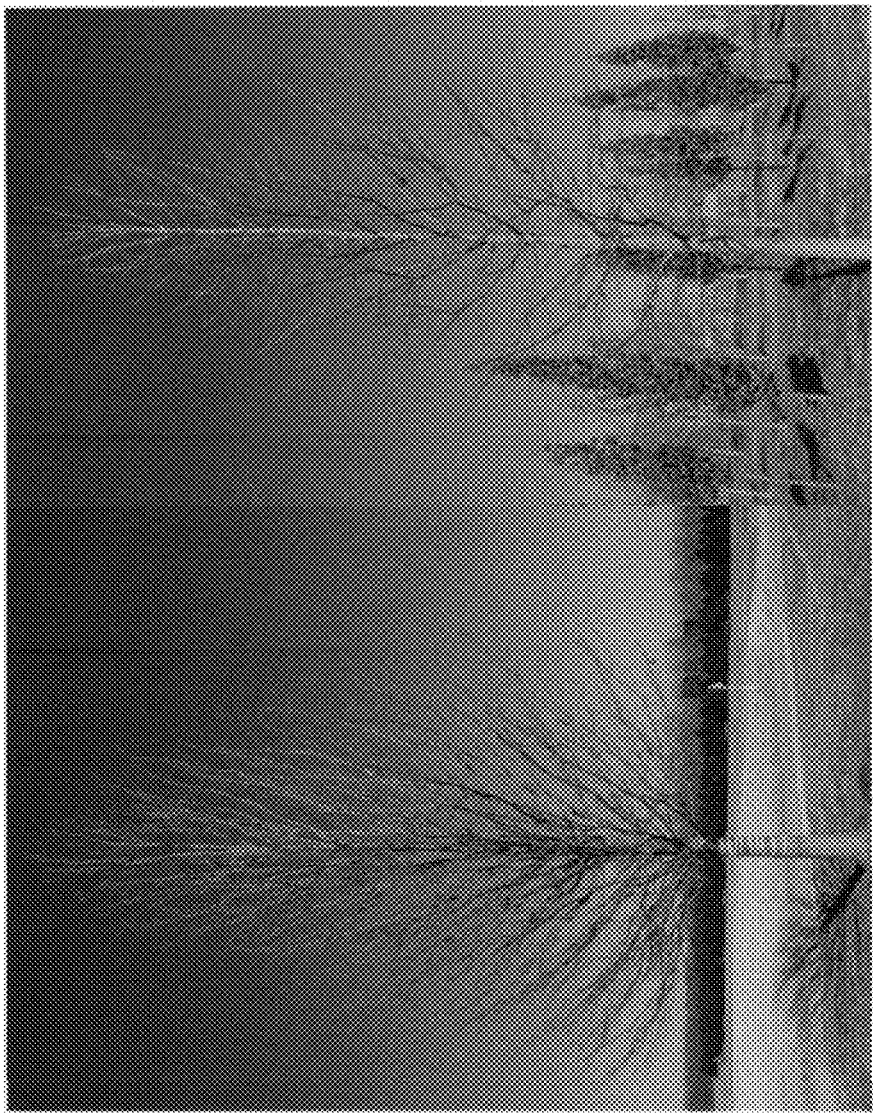

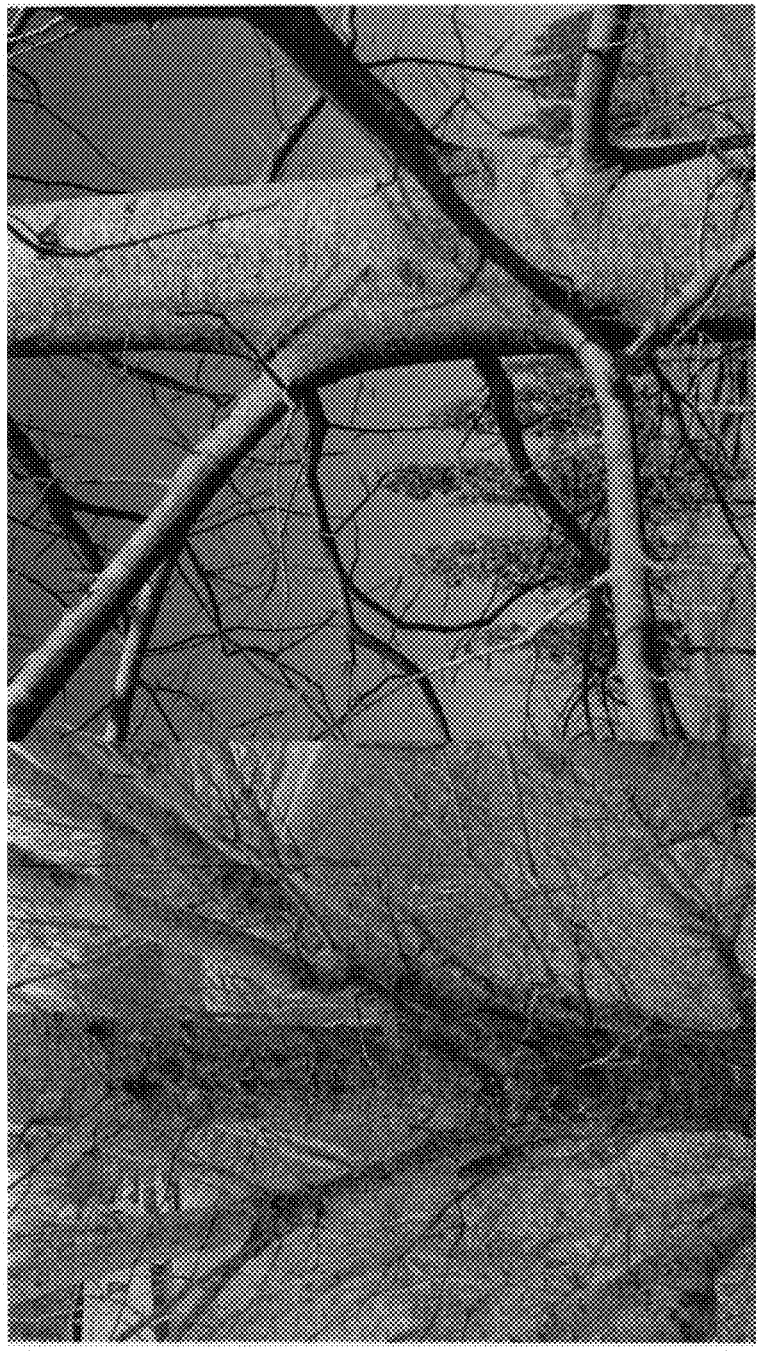

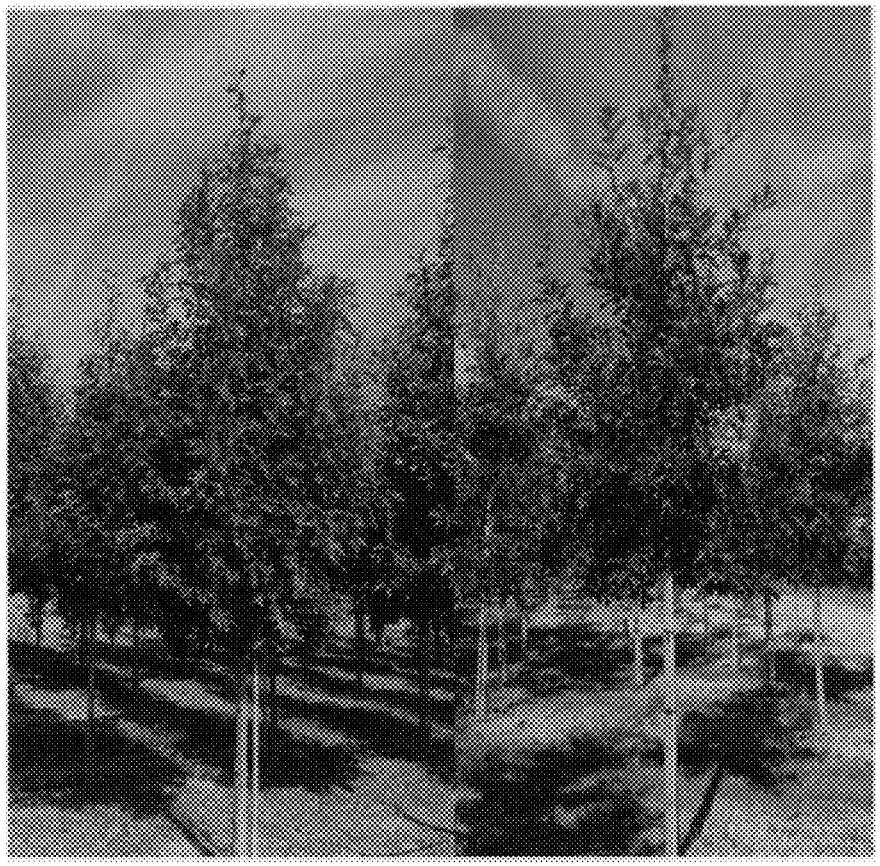

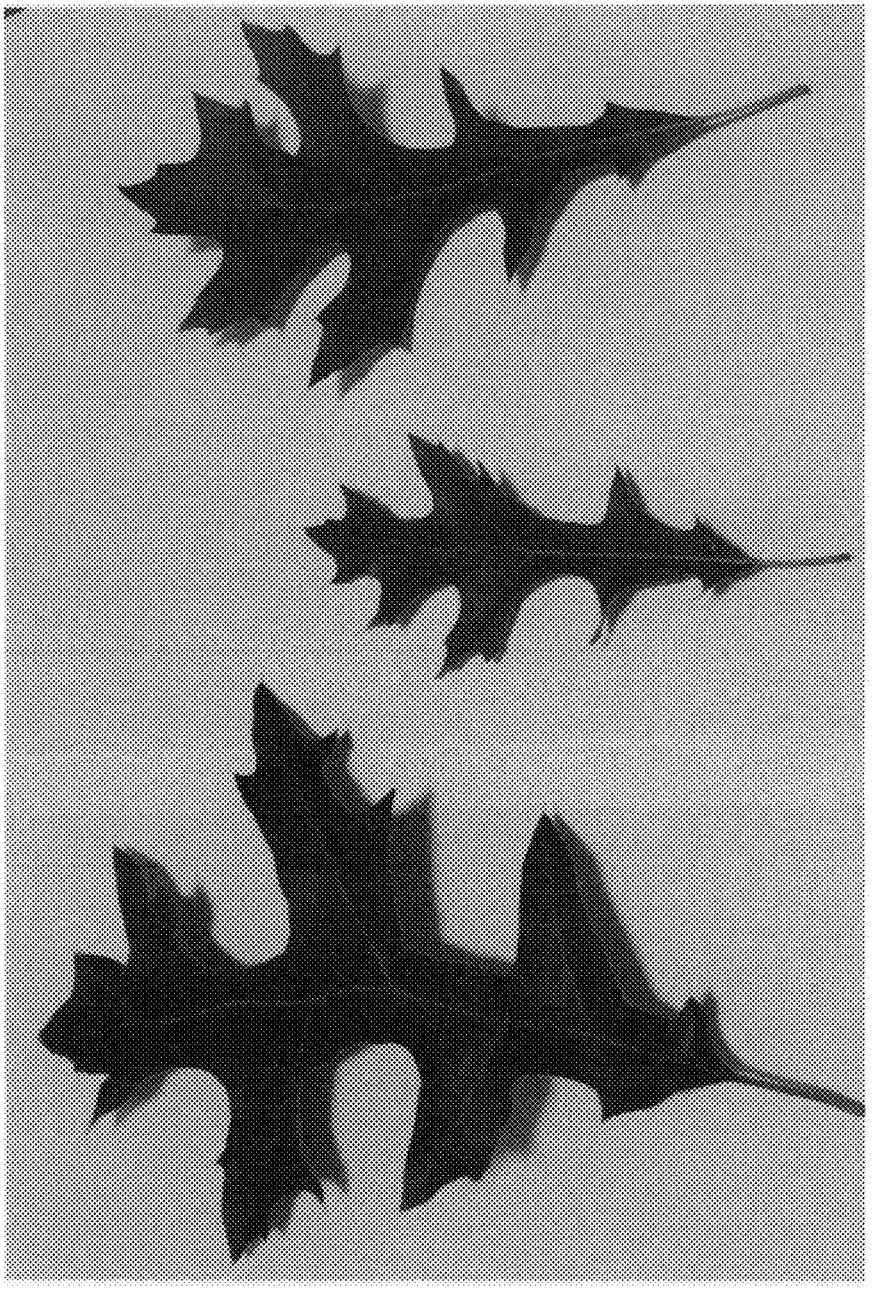

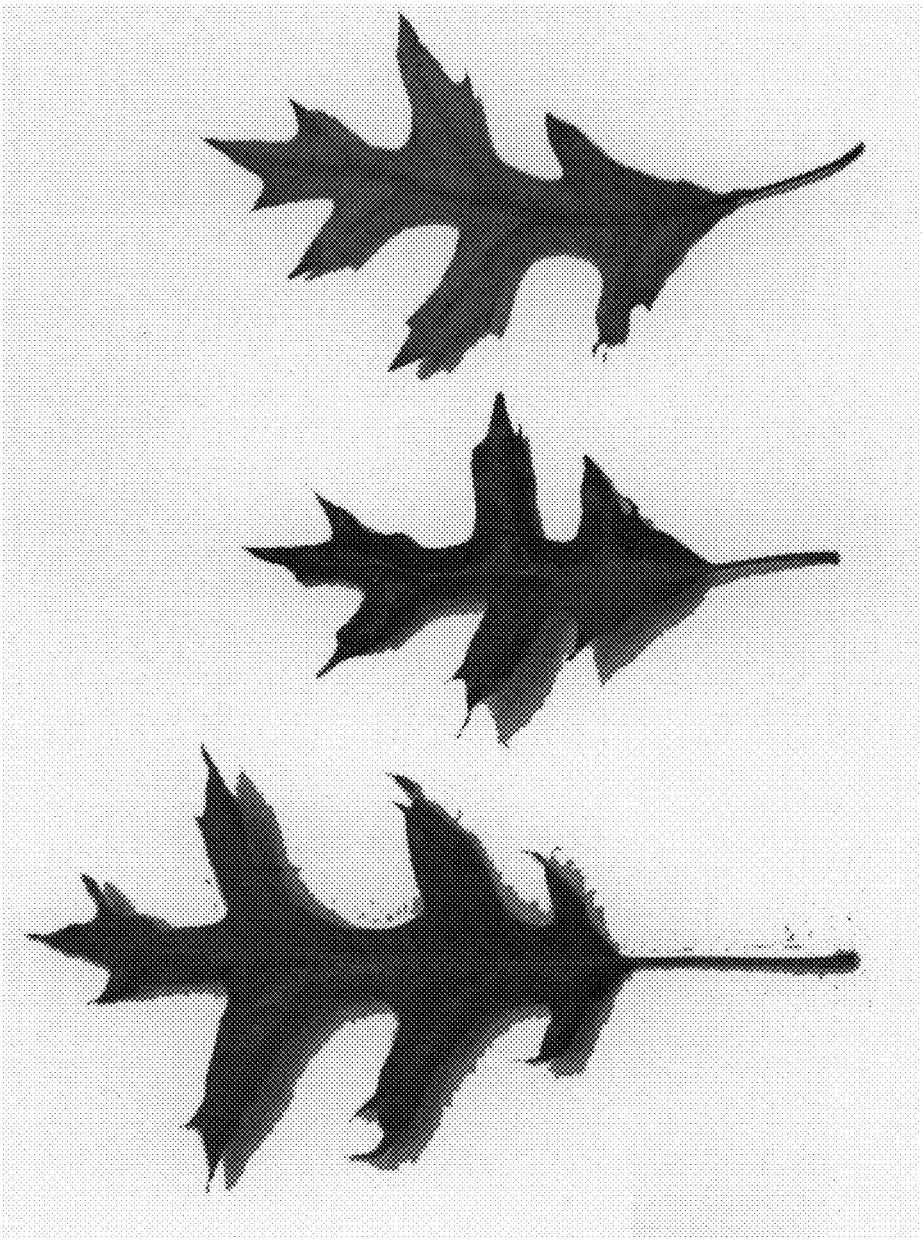

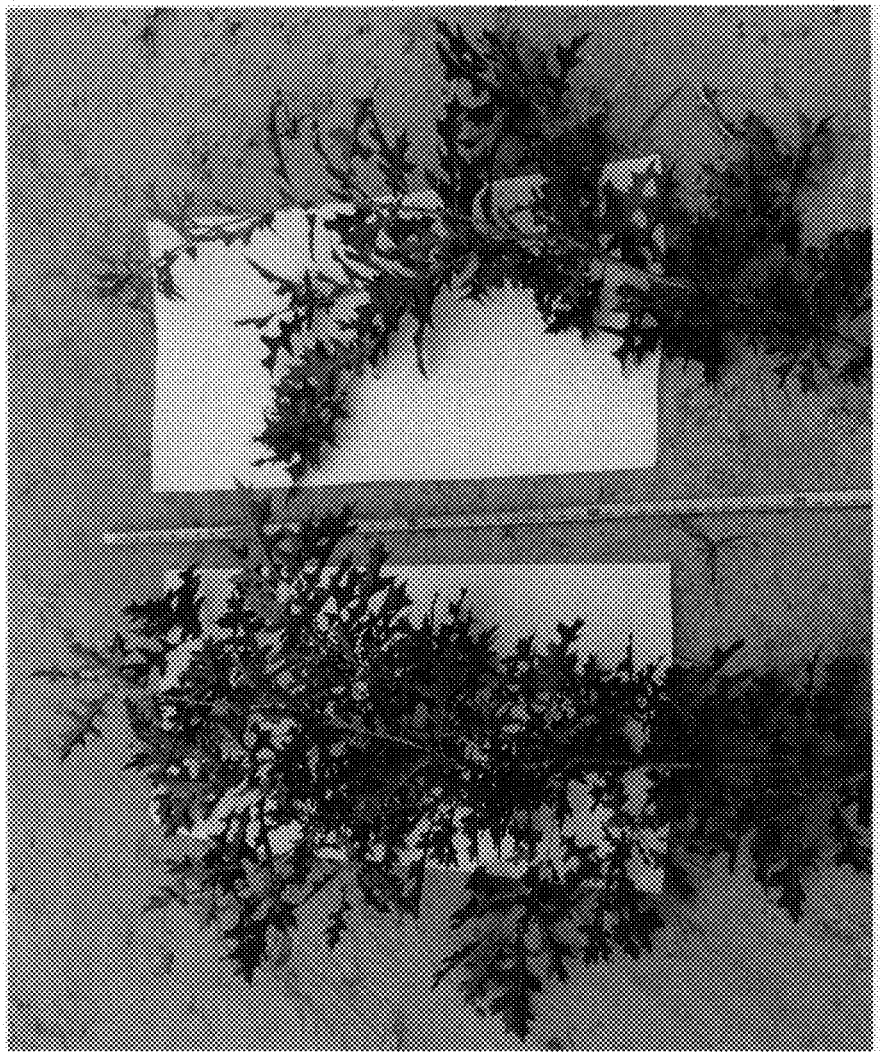

* * * * *